(12) United States Patent
Gerber et al.

(10) Patent No.: US 10,286,380 B2
(45) Date of Patent: May 14, 2019

(54) SORBENT POUCH

(71) Applicant: Medtronic, Inc., Minneapolis, MN (US)

(72) Inventors: Martin T. Gerber, Maple Grove, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 356 days.

(21) Appl. No.: 14/637,606

(22) Filed: Mar. 4, 2015

(65) Prior Publication Data
US 2015/0367052 A1 Dec. 24, 2015

Related U.S. Application Data

(60) Provisional application No. 62/016,613, filed on Jun. 24, 2014.

(51) Int. Cl.
*B01J 20/28* (2006.01)
*B01D 15/08* (2006.01)
*A61M 1/16* (2006.01)

(52) U.S. Cl.
CPC ........ *B01J 20/2805* (2013.01); *A61M 1/1696* (2013.01); *B01D 15/08* (2013.01); *B01J 20/28052* (2013.01); *A61M 1/1668* (2014.02); *A61M 2202/0057* (2013.01); *A61M 2205/121* (2013.01)

(58) Field of Classification Search
CPC .... A61M 1/14; A61M 1/1696; A61M 1/1668; A61M 2202/0057; A61M 2205/121; B01D 15/08; B01J 20/28052; B01J 20/2805

See application file for complete search history.

(56) References Cited

U.S. PATENT DOCUMENTS

| | | | |
|---|---|---|---|
| 3,608,729 | A | 9/1971 | Haselden |
| 3,669,880 | A | 6/1972 | Marantz |
| 3,776,819 | A | 12/1973 | Williams |
| 3,850,835 | A | 11/1974 | Marantz |
| 3,884,808 | A | 5/1975 | Scott |
| 3,902,490 | A | 9/1975 | Jacobsen et al. |
| 3,989,622 | A | 11/1976 | Marantz |
| 4,094,775 | A | 6/1978 | Mueller |
| 4,206,054 | A | 6/1980 | Moore |
| 4,209,392 | A | 6/1980 | Wallace |

(Continued)

FOREIGN PATENT DOCUMENTS

| | | |
|---|---|---|
| CN | 104936633 | 9/2015 |
| EP | 1701752 A2 | 9/2006 |

(Continued)

OTHER PUBLICATIONS

PCT/US2015/020044 International Search Report Written Opinion dated Jun. 30, 2015.

(Continued)

*Primary Examiner* — John Kim
(74) *Attorney, Agent, or Firm* — Kenneth Collier; Roger Hahn

(57) ABSTRACT

A sorbent pouch for use in sorbent dialysis. The sorbent pouch allows for fluid to freely pass into and through the sorbent materials, while keeping the sorbent materials inside the sorbent pouch.

18 Claims, 11 Drawing Sheets

(56) References Cited

U.S. PATENT DOCUMENTS

| | | |
|---|---|---|
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,684,460 A | 8/1987 | Issautier |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson et al. |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau et al. |
| 6,491,993 B1 * | 12/2002 | Forbes ............... B01J 20/28016 428/34.3 |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi |
| 7,776,210 B2 | 8/2010 | Rosenbaum |
| 7,794,419 B2 | 9/2010 | Paolini et al. |
| 7,850,635 B2 | 12/2010 | Polaschegg |
| 7,922,686 B2 | 4/2011 | Childers et al. |
| 7,922,911 B2 | 4/2011 | Micheli |
| 7,947,179 B2 | 5/2011 | Rosenbaum |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 11/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Hamada et al. |
| 8,404,491 B2 | 3/2013 | Ding et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 2001/0007931 A1 | 7/2001 | Blatter |
| 2001/0009756 A1 | 7/2001 | Hei et al. |
| 2002/0112609 A1 | 8/2002 | Wong |
| 2002/0117436 A1 | 8/2002 | Rajan |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0168963 A1 | 9/2004 | King |
| 2004/0257409 A1 | 12/2004 | Cheok |
| 2005/0006296 A1 | 1/2005 | Sullivan |
| 2005/0113796 A1 | 5/2005 | Taylor |
| 2005/0150832 A1 | 7/2005 | Tsukamoto |
| 2005/0274658 A1 | 12/2005 | Rosenbaum |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0051696 A1 | 2/2008 | Curtin |
| 2008/0053905 A9 | 3/2008 | Brugger et al. |
| 2008/0217245 A1 | 9/2008 | Rambod |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0157877 A1 | 6/2009 | Baek |
| 2009/0216045 A1 | 8/2009 | Singh |
| 2009/0266358 A1 | 10/2009 | Sacristan Rock |
| 2010/0004588 A1 | 1/2010 | Yeh |
| 2010/0007838 A1 | 1/2010 | Fujimoto |
| 2010/0078381 A1 | 4/2010 | Merchant |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0217181 A1 | 8/2010 | Roberts |
| 2010/0224492 A1 | 9/2010 | Ding et al. |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |

(56) References Cited

U.S. PATENT DOCUMENTS

| | | |
|---|---|---|
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| EP | 1592494 B1 | 6/2009 |
| EP | 1345856 B1 | 3/2013 |
| EP | 2344220 B1 | 4/2013 |
| EP | 1345687 | 6/2013 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | WO 20070103411 | 9/2007 |
| WO | 2008075951 | 6/2008 |
| WO | 2010028860 A1 | 2/2010 |
| WO | 2010141949 | 12/2010 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | WO 2013/019179 | 2/2013 |
| WO | WO 2013/028809 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | 2015142624 | 9/2015 |
| WO | 2015199764 | 12/2015 |

OTHER PUBLICATIONS

PCT/US2014/065950 International Search Report and Written Opinion dated Feb. 24, 2015.
PCT/US2015/032492 International Search Report dated Nov. 17, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 17, 2015.
PCT/US2015/020046 International Search Report and Written Opinion dated Jun. 29, 2015.
PCT/US15/18587 International Preliminary Report on Patentability Dated Jun. 6, 2016.
PCT/US2015/018587 International Search Report and Written Opinion Dated Jun. 25, 2015.
PCT/US2015/020044 International Search Report dated Jun. 30, 2015.
Office Action for Chinese Application No. 2015/80009562.5 dated Jul. 3, 2017.
International Preliminary Report on Patentability for Application No. PCT/US2015/032492 dated Jun. 30, 2017.
International Preliminary Report on Patentability for Application No. PCT/US2015/016273 dated Feb. 19, 2016.
European Search Report for App. No. 15751391.2 dated Aug. 4, 2017.
European Search Report and supplementary Search Report for App. No. 14865374.4 dated Jun. 12, 2017.

* cited by examiner

SORBENT POUCH

FIELD OF THE INVENTION

The invention relates to a sorbent pouch wherein the sorbent pouch contains at least one sorbent material, and the sorbent pouch is constructed such that fluid freely passes through the sorbent pouch while the sorbent materials remain inside the sorbent pouch.

BACKGROUND

One of the drawbacks of sorbent dialysis systems is high cost due to expensive sorbent materials. Disposing of cartridges housing sorbent materials after each use generates waste and also drives up costs. Known dialysate fluid circulation systems and apparatuses have separate housings where a first housing has a sorbent material capable of performing a first function such as releasing sodium into dialysate fluid flowing through the first housing, and a second housing having a material capable of performing another function such as binding sodium ions from dialysate fluid flowing through the second housing. However, such systems are not modular and customizable and are usually formed into a single housing design that limits flexibility and the possibility of customized use personalized to a particular patient. Such sorbent systems are one-size-fits-all and operate using similar amounts of sorbent materials across different treatment sessions regardless of the unique needs or dialysis parameters for a particular patient. Moreover, known sorbent systems do not provide for recharging some or all of the components of a sorbent cartridge that would allow reuse of specific components and enable lower long-term costs for operating such systems, nor ease of manufacturing the separate sorbent housings.

As such, there is a need for a sorbent cartridge having a separation of materials within the sorbent cartridge to allow for isolation of those materials. There is also a need for a sorbent cartridge providing for isolation of one or more sorbent materials to allow for cheaper or non-reusable materials to be discarded, while more expensive and reusable materials are recharged. As such, there is a need for a sorbent partition such as a sorbent pouch or a system of sorbent pouches that can allow dialysate to freely move into and out of the sorbent pouch while keeping the sorbent material inside. There is a need for a sorbent pouch that keeps the different sorbent materials separated from each other.

There is also a need for facilitating ease of packaging and shipping using a modular interchangeable system to house sorbent materials. There is a need for providing an option for allowing sub-vendors to manufacture sorbent housing or separate assembly line fill production facilities from one another. There is also a need for providing a customized sorbent system wherein different layers of sorbent materials can be used together wherein each sorbent pouch is modular and interchangeable. There is also a need for reducing final assembly steps required in preparing a dialysis system for use. To combat counterfeiting, there is a need for isolating individual vendors from a sorbent manufacturing process wherein specific sorbent materials used for dialysis can be pre-filled separately. There is also a need for pre-filling a component housing sorbent materials at precise quantities to avoid user error.

SUMMARY OF THE INVENTION

The first aspect of the invention relates to a sorbent pouch. In any embodiment of the first aspect of the invention, the sorbent pouch can comprise a porous material forming in-part a sorbent pouch containing at least one sorbent material wherein the porous material can allow fluid to pass through the sorbent pouch.

In any embodiment of the first aspect of the invention, the porous material can allow fluid to pass through the pouch and can substantially retain the at least one sorbent material in the sorbent pouch.

In any embodiment of the first aspect of the invention, the porous material can retain greater than 98% by weight of the sorbent material in the sorbent pouch. In any embodiment of the first aspect of the invention, the porous material can allow fluid to pass through the sorbent pouches but can retain anywhere from at least 70%, 75%, 80%, 85%, 90%, 92%, 93%, 94%, 95%, 96%, or 97% by weight of one sorbent material in the sorbent pouch.

In any embodiment of the first aspect of the invention, the sorbent pouch can contain a sorbent material selected from activated carbon, hydrous zirconium oxide, urease, alumina, zirconium phosphate and ion-exchange resin, or combinations thereof.

In any embodiment of the first aspect of the invention, the sorbent pouch can contain glass beads.

In any embodiment of the first aspect of the invention, the sorbent pouch can contain solid urease and the porous material can allow fluid containing dissolved urease to pass through the sorbent pouch material so that it can be become immobilized to another sorbent material, such as alumina.

In any embodiment of the first aspect of the invention, the porous material can be selected from any one of bolting cloth, porous polymer, porous metal, cotton, ashless filter paper, Dacron and polyethylene terephthalate.

In any embodiment of the first aspect of the invention, the sorbent pouch can contain two or more sorbent materials.

In any embodiment of the first aspect of the invention, the sorbent pouch can contain two or more sorbent materials mixed together.

In any embodiment of the first aspect of the invention, the sorbent pouch can have any geometric shape. In any embodiment of the first aspect of the invention, the shape can be selected from the group consisting of a circular shape, a square shape, a rectangular shape, a triangular shape, or a disc shape.

In any embodiment of the first aspect of the invention, the sorbent pouch can be shaped to be adapted into an internal cavity defined by a sorbent cartridge in which the sorbent pouch is housed.

In any embodiment of the first aspect of the invention, the sorbent pouch can have a semi-rigid structure.

In any embodiment of the first aspect of the invention, the sorbent pouch can have a porous structure.

In any embodiment of the first aspect of the invention, the sorbent pouch can have a rigid structure.

In any embodiment of the first aspect of the invention, the sorbent pouch can further comprise side portions constructed from a fluid impermeable material.

In any embodiment of the first aspect of the invention, the porous material can be impregnated with an antimicrobial substance and/or an anticoagulant.

In any embodiment of the first aspect of the invention, the sorbent pouch can further comprise an o-ring seal member disposed on an outer periphery of the pouch.

In any embodiment of the first aspect of the invention, at least one portion of the sorbent pouch can comprise a double layer of the sorbent pouch material.

In any embodiment of the first aspect of the invention, the sorbent pouch can be opened and re-sealed.

In any embodiment of the first aspect of the invention, the sorbent pouch can further comprise an elastomeric material disposed on a side portion of the pouch.

Any of the features disclosed as being part of the first aspect of the invention can be included in the first aspect of the invention, either alone or in combination.

The second aspect of the invention is directed to a sorbent pouch system. In any embodiment of the second aspect of the invention, the sorbent pouch system can comprise one or more sorbent pouches wherein the one or more sorbent pouches can be formed from a porous material and can contain inside at least one sorbent material. In any embodiment of the second aspect of the invention, the one or more sorbent pouches can be capable of being attached and/or detached from each other. In any embodiment of the second aspect of the invention, the porous material can allow fluid to pass through the one or more sorbent pouches but can substantially retain at least one sorbent material from passing out of the one or more sorbent pouches In any embodiment of the second aspect of the invention, the porous material can retain greater than 98% by weight of the sorbent material.

In any embodiment of the second aspect of the invention, the sorbent pouch system can have sorbent material selected from the group consisting of activated carbon, hydrous zirconium oxide, zirconium phosphate, ion-exchange resin, alumina, urease, and combinations thereof.

In any embodiment of the second aspect of the invention, the sorbent material can be urease, and the porous material can allow fluid containing dissolved urease to pass through the pouch.

In any embodiment of the second aspect of the invention, any one of the one or more sorbent pouches can contain two or more sorbent materials.

In any embodiment of the second aspect of the invention, the at least one sorbent materials can be mixed together.

In any embodiment of the second aspect of the invention, the sorbent pouch can comprise a separator that separates the sorbent pouch into a top portion and a bottom portion. The separator can allow liquid to pass through the separator but can prevent any of the sorbent materials from passing through the separator. In any embodiment of the second aspect of the invention, the top portion of the sorbent pouch can contain at least one sorbent material, and the bottom portion of the sorbent pouch can contain at least one sorbent material. In any embodiment of the second aspect of the invention, the at least one sorbent material contained in the bottom portion of the sorbent pouch can be different from the at least one sorbent material contained in the top portion of the sorbent pouch.

In any embodiment of the second aspect of the invention, the sorbent pouch can comprise more than one separator.

In any embodiment of the second aspect of the invention, the sorbent pouch system can have a sorbent pouch containing alumina and also a sorbent pouch containing urease, wherein the sorbent pouch containing urease is constructed of a porous material that allows fluid to pass through the sorbent pouch and also allows dissolved urease to pass through the sorbent pouch material to become bound to an enzyme immobilizing sorbent material.

In any embodiment of the second aspect of the invention, the one or more sorbent pouches can each comprise sidewalls having a thickness different from that of the other sorbent pouches, such that the one or more sorbent pouches have differing interior diameters.

In any embodiment of the second aspect of the invention, the one or more pouches can be placed in series, such that each pouch has a sidewall thickness greater than that of the previous pouch in series.

In any embodiment of the second aspect of the invention, the one or more sorbent pouches can each have a differing exterior diameter from the other pouches.

In any embodiment of the second aspect of the invention, the one or more pouches can be placed in series, such that each pouch has an exterior diameter smaller than that of the previous pouch in series.

In any embodiment of the second aspect of the invention, the one or more pouches can each contain one or more annular ring, wherein the one or more annular ring can be constructed from a fluid impermeable substance. In any embodiment of the second aspect of the invention, the annular ring can be disposed on the interior circumference of the sorbent pouch and can extend radially into the center of the sorbent pouch.

In any embodiment of the second aspect of the invention, the annular ring can have a cross-sectional shape selected from the group comprising circular, rectangular and triangular.

Any of the features disclosed as being part of the second aspect of the invention can be included in the second aspect of the invention, either alone or in combination.

DETAILED DESCRIPTION OF THE INVENTION

Figure 1:
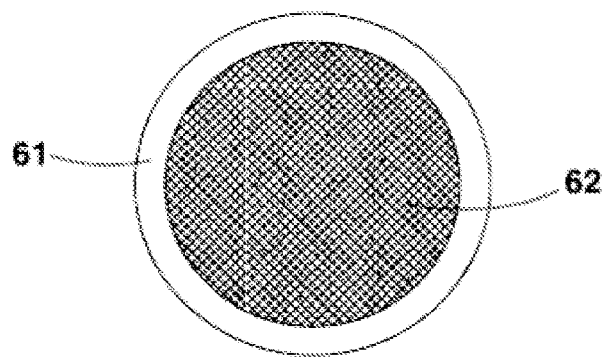
FIG. 1 is a top view of a disc-shaped sorbent pouch.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "adhesive" is any substance known in the art for use in affixing one surface to another surface, or to seal two surfaces together.

An "annular ring" is a ring having a substantially circular shape. The cross-section of the ring may be rectangular, triangular, round, or any other known shape. The ring may be constructed of any rigid or semi-rigid material, and may be adhered to the inner surface of a sorbent pouch by any means known in the art. An annular ring may also be an "o-ring."

The term "cartridge" refers to any container designed to contain a powder, fluid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

A "circular shape" describes a sorbent pouch constructed in a generally round shape having the form of a circle. This term is not intended to limit the shape of the sorbent pouch to any particular size or dimensions, and may encompass oval or oblong configurations as well.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "disc-like shape" describes a sorbent pouch forming a flat, circular shape, as in a compressed cylinder. This definition is not intended to limit the dimensions or radius of the sorbent pouch, and may therefore encompass discs having an oval shape, and discs of any radial width or thickness.

A "double layer of material" describes a second layer of material of the same or smaller area than the primary layer of material, disposed on the surface of the primary layer of material forming a surface of a sorbent pouch. The material used to form the double layer can be the same or different from the material forming the primary layer. Any rigid or flexible porous material known in the art is contemplated.

An "elastomer" or "elastomeric material" is a material comprising a polymer having high elasticity, such that the material may be easily stretched and shaped to be adapted to an internal cavity defined by a sorbent cartridge.

"Engagement members" allow compartments to cooperatively engage. In certain embodiments, these engagement members may be clasps or latches. In one embodiment, an engagement member allows for coupling of a top portion and a bottom portion of a sorbent pouch that can be opened and resealed.

"Flow" refers to the movement of a fluid or gas.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

A "fluid impermeable material" is any material through which fluid cannot pass.

The term "fluidly connectable" refers to the ability of providing for the passage of fluid or gas from one point to another point. The two points can be within or between any one or more of compartments, modules, systems, components, pouches and rechargers, all of any type.

A "geometric shape" refers any geometric shape in Euclidean and other geometries such as a rectangle, disc, triangle, or polygon inter alia. In reference to a sorbent pouch as described in the invention, the geometric shape can refer to one or more side of the sorbent pouch wherein a rectangular sorbent pouch can be generally constructed to have a rectangular shape at least on one side to form a porous sealed bag.

The term "immobilized urease" refers to urease that has been adsorbed onto a solid material, such as alumina.

The term "immobilizing sorbent material" refers to the process of a sorbent material being placed onto another material, such that the sorbent material is held in place by some force. The force may be provided by absorption, adsorption, adhesion, or any other method for the chemical to be held in place.

The term "impregnated" describes any process known to a person of ordinary skill in the art by which a material may be caused to absorb or be saturated with a substance. In one embodiment, the material forming a sorbent pouch may be impregnated with an anticoagulant, such that the surface of the sorbent pouch absorbs the anticoagulant. "Infusate" is a solution of one or more salts for the adjustment of the composition of a dialysate.

The term "in-part" describes a portion up to and including one hundred percent. For example, a component formed in-part by a material means that the material forms at least some portion of the component, and that the material may form up to the entire component.

An "o-ring seal member" is a mechanical gasket having a ring shape; it is a loop of elastomer or other suitable material known in the art with a round cross-section, designed to be seated in a groove and compressed during assembly between two or more parts, creating a seal at the interface. In one embodiment, an o-ring seal member may be used to seal the interface between a sorbent pouch and a sorbent cartridge such that fluid is directed through, rather than around, the sorbent pouch.

A "porous material" may describe any suitable porous material known in the art from which a sorbent pouch may be constructed. For example, the porous material can include, but is not limited to, bolting cloth, porous polymer, porous metal, cotton, ashless filter paper, Dacron and polyethylene terephthalate. The porous material chosen for individual sorbent pouches may be selected based upon specific porosity in view of the sorbent material to be contained within the sorbent pouch.

A "porous structure" describes a sorbent pouch being formed of a porous material, wherein the sorbent pouch can be manipulated to fit an internal cavity defined by a sorbent cartridge.

A "pouch" is any in-part porous container, having any shape and being made of any material as described below, containing at least one sorbent material and allowing fluid to pass through the pouch. For example, a pouch may have a disc-like shape, having rigid side walls and porous, flexible upper and lower surfaces, such that fluid is allowed to flow through the lower and upper surfaces of the pouch, but does not pass through the side walls of the pouch. Alternatively, the pouch may be rectangular or triangular in shape. The pouch may be made entirely of flexible porous material, or may be formed of entirely rigid, partially porous material.

The pouch may be formed in dimensions correlating directly to the cartridge into which the pouch is inserted, such that the edges of the pouch are flush with the interior surface of the cartridge. Alternatively, the pouch may be formed of a flexible material with dimensions slightly larger than those of the interior of the cartridge, such that a seal is formed between the pouch and the interior surface of the cartridge. In another embodiment, the pouch may be formed in dimensions smaller than that of the interior of the cartridge, such that the pouch may be simply placed in the cartridge. A pouch may be formed of bolting cloth, porous polymer, porous metal, cotton, ashless filter paper, Dacron, polyethylene terephthalate, or any other flexible or rigid, permeable or semi-permeable material.

A "rigid structure" describes a sorbent pouch being formed of inflexible material such that the sorbent pouch cannot be manipulated and reshaped to be adapted to an internal cavity defined by a sorbent cartridge, but instead maintains its shape.

A "semi-rigid structure" describes a sorbent pouch having a combination of rigid and flexible surfaces. For example, a sorbent pouch having a disc-like shape may have a rigid outer circumference, with flexible top and bottom surfaces. Other combinations are also available.

A "sensor" is a component capable of determining the states of one or more variables in a system. In one embodiment, a sensor may be capable of sensing the presence and/or concentration of at least one compound in the fluid flowing through at least one sorbent pouch, using any means known in the art.

A "separator" is a layer of flexible or rigid material positioned within a sorbent pouch that divides the sorbent pouch into top and bottom portions, such that sorbent materials housed in the top and bottom portions, respectively, do not come in contact with each other. The separator is formed of a porous material such that spent dialysate or other fluid may flow between the top and bottom portions of the sorbent pouch through the separator, but such that the sorbent materials housed in the top and bottom portions of the sorbent pouch cannot pass through the separator. Any given pouch may contain one or more separator.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Sorbent materials" are materials capable of removing specific solutes from solution, such as urea or urea byproducts.

The term "sorbent pouch" refers to a structure that contains at least one sorbent material, and is constructed from a material that can allow fluid to freely pass through the sorbent pouch while substantially retaining the sorbent material inside.

"Spent dialysate" is a dialysate contacted with blood through a dialysis membrane and contains one or more impurity, or waste species, or waste substance, such as urea.

A "square" or "rectangular" shape describes a sorbent pouch having four edges and four angles. This description is not intended to limit the size and dimensions of the sorbent pouch, and may therefore encompass sorbent pouches having corners with angles greater than or less than ninety degrees, and with edges of differing lengths with respect to each other.

The term "substantially" is used in conjunction with a term to describe a particular characteristic. For example, as used in the phrase "substantially retains the at least one sorbent material in the sorbent pouches," the term describes the ability to retain a sorbent material or particles characterized by an average pore diameter such that a significant amount of the material or particles are retained within the sorbent pouch.

A "triangular shape" describes a sorbent pouch having three edges and three corners, wherein the edges and corners may vary in length and degree individually and with respect to each other.

Sorbent Pouches

The present invention utilizes separate sorbent pouches that contain individual portions of sorbent material, or multiple layers of sorbent material. The sorbent pouches are designed such that spent dialysate or water may pass through the pouch and into the sorbent material or materials within, and the spent dialysate or water may then pass out of the sorbent pouch, while the sorbent materials remain inside the sorbent pouch.

The sorbent pouches of the invention can be constructed in any shape. For convenience, they are often drawn as circular or disc shaped. However, any of the described embodiments of the invention can be made in any shape, including triangular, rectangular, etc.

Figure 2:
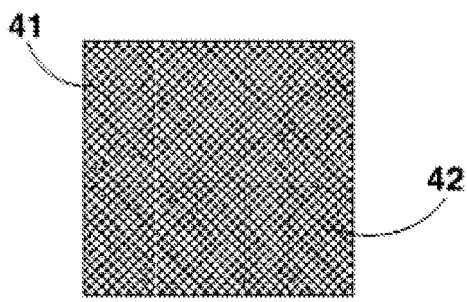
FIG. 2 is a top view of a rectangular sorbent pouch.

For example, FIG. 1 depicts a disc-shaped sorbent pouch 61 containing sorbent material 62, whereas FIG. 2 shows a rectangular sorbent pouch 41 containing sorbent material 42. The sorbent pouches may be constructed of any known material, including bolting cloth, porous polymer, porous metal, cotton, ashless filter paper, nylon, Dacron, and polyethylene terephthalate as described herein, and each may be constructed in any shape.

Figure 3:
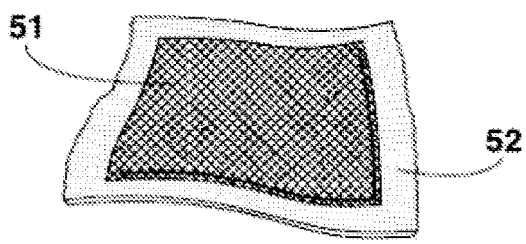
FIG. 3 is a perspective view of a rectangular sorbent pouch.

In one embodiment, the sorbent pouches of the invention can be configured as shown in FIG. 2. The sorbent pouch 41 can be constructed of a material that can allow fluid to pass through the sorbent pouch 41, but will not allow the sorbent material 42 contained within the sorbent pouch 41 to pass out of the sorbent pouch 41. The sorbent material 42 can be placed loosely within the sorbent pouch 41, allowing the sorbent material 42 to move within the sorbent pouch 41, but not to travel out of the sorbent pouch 41. The sorbent pouch 41 can be made in any size or shape. In some embodiments, as shown in FIGS. 2 and 3, the sorbent pouch can be roughly rectangular shaped. In another embodiment, as shown in FIG. 1, the sorbent pouch 61 can be disc-shaped. In any embodiment, the sorbent pouch can be shaped to be adapted into an internal cavity defined by a sorbent cartridge. In this way, the sorbent pouch may fit in the space, such that there may be void space, but such that the sorbent pouch generally fits the space. For example, a sorbent cartridge having a cylindrical internal cavity can accommodate a circular or disc-shaped sorbent pouch, while a sorbent cartridge having a conical internal cavity could accommodate a triangular sorbent pouch, and a sorbent cartridge having a square or rectangular internal cavity could accommodate a square or rectangular sorbent pouch.

FIG. 3 shows a rectangular sorbent pouch embodiment in which the sorbent material is contained in a raised inner portion of the sorbent pouch 51, while the outer perimeter of the sorbent pouch, having a serrated edge 52, is sealed by any means known in the art, including heat or pressure stamping, sewing, or adhesive sealing. The outer serrated edge 52 of the sorbent pouch may be permanently sealed, or may alternatively be resealable, such that the sorbent pouch may be opened and reclosed. For example, the serrated edge 52 may be sealed with a resealable adhesive, hook and loop fasteners (not shown), or with interlocking ridges (not shown) that may be separated and reclosed by the user. Optionally, a latch member (not shown) may be included on the serrated edge 52 of the sorbent pouch to provide additional strength in sealing the sorbent pouch. In some embodiments, the outer edge may simply be a folded edge. In use, compression from the other materials within a sorbent cartridge can keep the folded edge sealed and the sorbent materials inside the sorbent pouch. Alternatively, the sorbent pouch may be sealed with drawstrings that when tightened create a seal.

In some embodiments, the sorbent pouches can be formed from a material that is flexible. In general, the material is porous and allows fluid to pass through the sorbent pouches such that substantially all of the sorbent material or particles are retained by the material. Sorbent materials are generally formed from a solid substance that adsorbs and/or absorbs other substances. In other embodiments, the material forming the sorbent pouches can allow fluid to pass through the sorbent pouches but substantially retain the sorbent material in the sorbent pouch. In yet other embodiments, the material forming the sorbent pouches can allow fluid to pass through the sorbent pouches but retain at least 98% by weight of one sorbent material in the sorbent pouch. In still yet other embodiments, the material forming the sorbent pouches can allow fluid to pass through the sorbent pouches but can retain anywhere from at least 70%, 75%, 80%, 85%, 90%, 92%, 93%, 94%, 95%, 96%, or 97% by weight of one sorbent material in the sorbent pouch.

In some embodiments, the pore size of one or more of the sorbent pouches may be large enough so that the sorbent material can leave the sorbent pouch. For example, a sorbent pouch containing solid urease may be made with a pore size at a sufficient porosity to allow dissolved urease, or in certain embodiments, undissolved urease, to travel through the sorbent pouch material. The urease in such embodiments can be dissolved by a fluid as it passes through the sorbent pouch during priming of the sorbent cartridge prior to dialysis whereupon the urease can exit the sorbent pouch. The urease in solution can then contact a sorbent pouch containing immobilized alumina, where the urease will become bound to the alumina in the alumina sorbent pouch. Alternatively, the sorbent cartridge can contain a sorbent pouch containing alumina, and a solution of urease can be injected into the flow path before the sorbent cartridge. The urease solution can enter the sorbent pouch containing alumina, where the urease will become bound to the alumina in the alumina sorbent pouch. However, in other embodiments, it may be desirable to retain the dissolved urease in the sorbent pouch and as such the sorbent pouch is constructed from a material that substantially retains the urease within the sorbent pouch. In any embodiment, the sorbent assembly can comprise two or more sorbent pouches stacked in series.

The size of the sorbent pouches can vary in the invention. Because different amounts of each sorbent material may be required for a dialysis session, the sorbent pouches of the present invention may be in multiple sizes. In any sorbent pouch, glass beads can be incorporated into the sorbent material to facilitate flow.

The sorbent pouches may be constructed of a flexible or rigid material. The flexible material can be selected from any non-toxic material suitable for the intended use in a dialysis wherein the material can allow fluid to pass through the material yet substantially retain the sorbent material in the sorbent pouch. The flexible material can be selected from materials that have the appropriate porosity, strength and durability. When the material is selected for use with urease, alumina may also be provided in the sorbent pouch. Because the alumina will adsorb the urease, and keep the urease from flowing out of the sorbent pouch, the flexible material need only substantially retain the alumina.

In some embodiments, the sorbent pouches may be constructed out of both a flexible and a rigid material. For example, the top and bottom of the sorbent pouch may be constructed from a flexible material having a particular porosity to allow fluid flow, while the sides of the sorbent pouch may be constructed from a rigid material to define a particular shape such as a disc. In one embodiment, the sorbent pouches can be constructed of a material such as a porous polymer. The polymer may be made porous by creating small holes or pores in an otherwise solid polymer material. The polymer may be constructed from polyethylene terephthalate, high density polyethylene, low density polyethylene, polyvinyl chloride, polypropylene, polystyrene, or any other polymer known in the art.

In embodiments where the sorbent pouch is made of fabric, the weave of the fabric can have a specified porosity suitable for use with the sorbent material described herein for the intended use of dialysis. The pores of the sorbent pouch material must be large enough to allow the spent dialysate to freely travel into and out of the sorbent pouch, while at the same time must be small enough to keep the particles of the sorbent material inside the sorbent pouch. For this reason, sorbent pouches with different pore or mesh sizes can be utilized for different material layers. In another embodiment, the sorbent pouch may be made out of a natural fiber, such as cotton. In still other embodiments, the sorbent pouch may be constructed from ashless filter paper. The sorbent pouches may also be constructed out of a synthetic material such as Dacron, or polyethylene terephthalate.

Figure 4A:
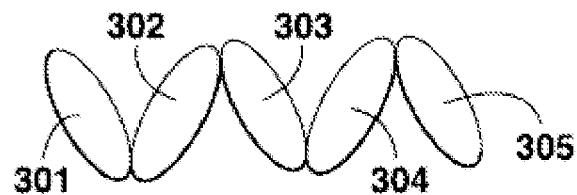
FIG. 4a is a side view of a string of disc-shaped sorbent pouches.
Figure 4B:
FIG. 4b is a top view of a string of disc-shaped sorbent pouches.
Figure 4C:
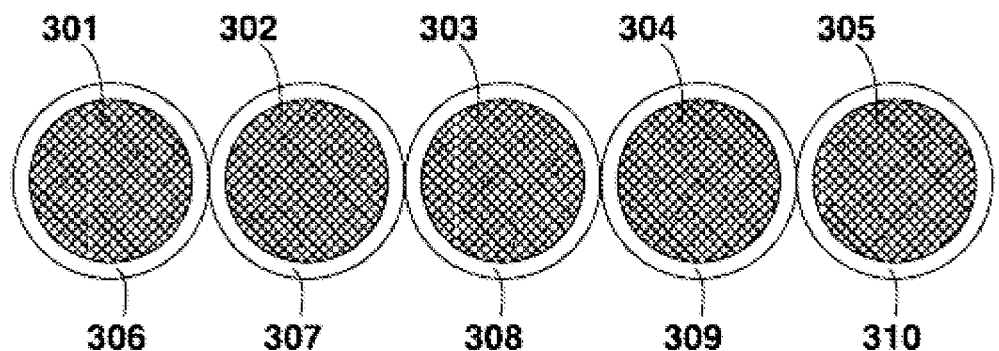
FIG. 4c is a top view of a string of disc-shaped sorbent pouches showing the detail of the outer edges of the sorbent pouches.
Figure 4D:
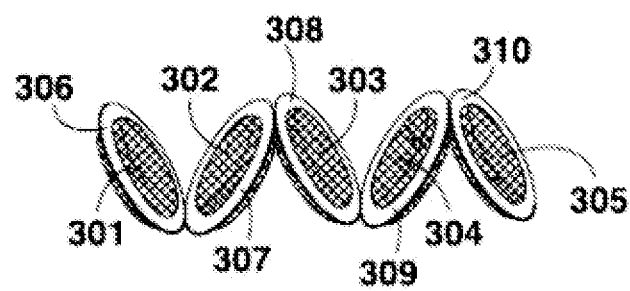
FIG. 4d is a perspective view of a string of disc-shaped sorbent pouches showing the detail of the outer edges of the sorbent pouches.
Figure 5A:
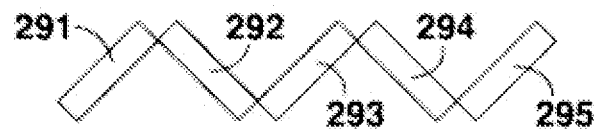
FIG. 5a is a side view of a string of rectangular sorbent pouches.
Figure 5B:
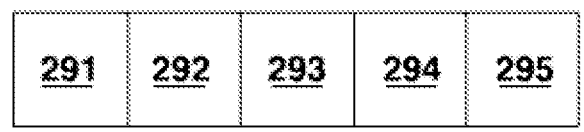
FIG. 5b is a top view of a string of rectangular sorbent pouches.
Figure 5C:
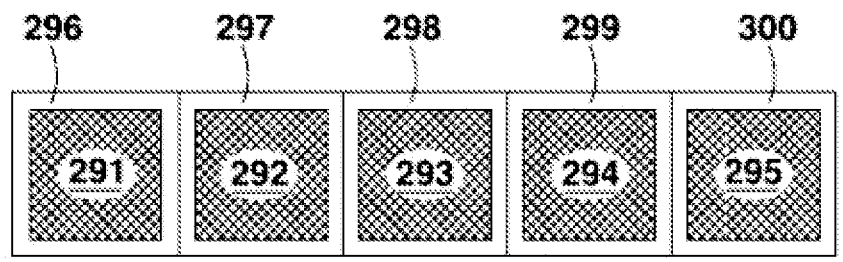
FIG. 5c is a top view of a string of rectangular sorbent pouches showing the detail of the outer edges of the sorbent pouches.

In any embodiment, multiple sorbent pouches may be connected as a string of sorbent pouches, as shown in FIGS. 4a, 4b, 4c, 4d, 5a, 5b and 5c. For example, as shown in FIGS. 4a, 4b and 4c, the individual sorbent pouches 301-305 may be permanently or separably connected directly, or may be connected at their outer edges 306-310 by any means known in the art, including by perforations in the material forming the outer edges 306-310. The individual sorbent pouches 301-305 comprising the string of sorbent pouches may be composed of the same material; may be composed of different materials such that each sorbent pouch in the string of sorbent pouches is composed of a different material; or may be composed of different materials such that some sorbent pouches in the string of sorbent pouches are composed of the same material, while others are composed of different materials, and are arranged in a random or repeating pattern. The materials of which the individual sorbent pouches are composed may be selected with particularity to the sorbent material housed inside the sorbent pouch. For example, sorbent pouches containing activated carbon may require a larger mesh to prevent the larger particles from escaping the sorbent pouch. By contrast, sorbent pouches containing hydrous zirconium oxide may require a smaller mesh to prevent the smaller particles from escaping the sorbent pouch. Any combination of sorbent pouch materials and mesh sizes among the string of sorbent pouches, and any number of individual sorbent pouches making up the string of sorbent pouches, is envisioned. Additionally, the interior portion of the sorbent pouches containing the sorbent material 301-305, though shown in FIG. 4c as circular, may be constructed in any shape, including but not limited to, rectangular, as shown in FIG. 5c, wherein both the interior portion of the sorbent pouches containing the sorbent material 291-295 and the outer edges of the sorbent pouches 296-300 are shown having a rectangular shape.

Figure 6:
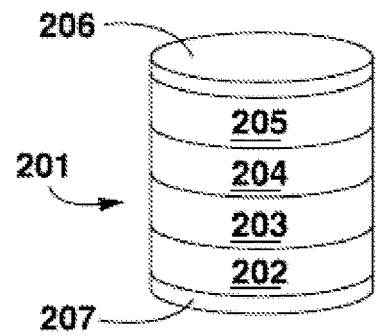
FIG. 6 is a perspective view of a sorbent cartridge comprising a stacked assembly of sorbent pouches containing activated carbon, hydrous zirconium oxide, urease, alumina, and zirconium phosphate.

One non-limiting embodiment of the invention is shown in FIG. 6. The sorbent cartridge 201 can comprise multiple sorbent pouches 202-205, including a sorbent pouch containing activated carbon 202, a sorbent pouch containing hydrous zirconium oxide 203, a sorbent pouch containing alumina/urease 204, and a sorbent pouch containing zirconium phosphate 205. In other embodiments, alumina can be contained in one sorbent pouch and urease in another sorbent pouch (not shown). Spent dialysate can enter through the bottom surface 207 of the sorbent cartridge 201, and flow through each of the sorbent pouches 202-205 sequentially, and then flow out of the sorbent cartridge 201 through the top surface 206 of the sorbent cartridge 201. In this way, the spent dialysate can come into contact with each sorbent material layer, while each sorbent material layer is kept separate from each of the other layers. One skilled in the art will understand that the sorbent pouches may be arranged in alternate orders and still be within the scope of the invention. For example, the first sorbent pouch 202 may contain activated carbon, the second sorbent pouch 203 may contain alumina/urease, the third sorbent pouch 204 may contain hydrous zirconium oxide, and the fourth sorbent pouch 205 may contain zirconium phosphate. In another embodiment, the first sorbent pouch 202 may contain activated carbon, the second sorbent pouch 203 may contain alumina/urease, the third sorbent pouch 204 may contain zirconium phosphate and the fourth sorbent pouch 205 may contain hydrous zirconium oxide. The precise order of the sorbent pouches within the sorbent cartridge is not critical to the invention, so long as the sorbent pouch containing zirconium phosphate is located downstream of the sorbent pouch containing alumina/urease. In some embodiments, a sorbent pouch can contain multiple sorbent materials, either arranged in layers or alternatively intermixed within the sorbent pouch. Additionally, any number of sorbent pouches arranged sequentially in the sorbent cartridge is envisioned.

Figure 14:
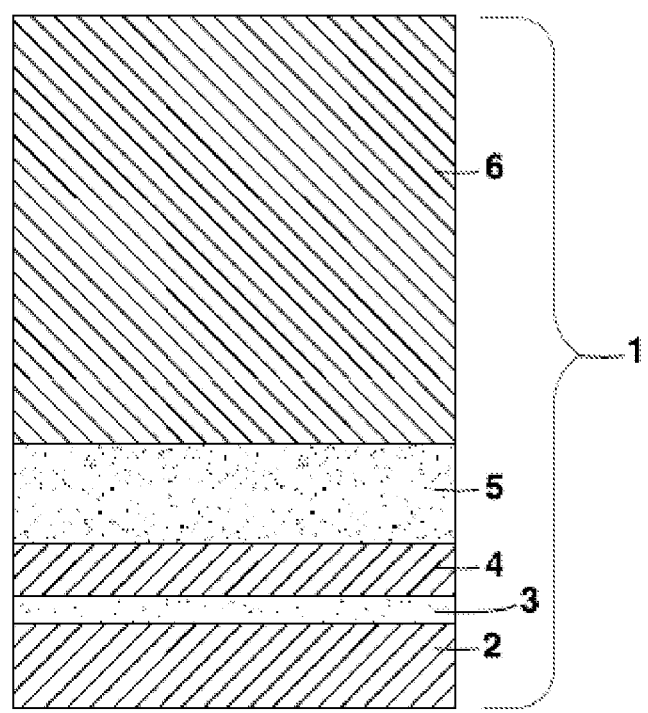
FIG. 14 shows an exemplary sorbent cartridge containing activated carbon, hydrous zirconium oxide, urease, alumina, and zirconium phosphate.

One non-limiting exemplary sorbent cartridge is shown in FIG. 14. Spent dialysate or fluid can flow from the bottom of the sorbent cartridge 1 to the top of the cartridge. The first sorbent material the spent dialysate or fluid contacts can be activated carbon 2. Activated carbon 2 will remove nonionic toxins from the fluid by adsorption. Creatinine, glucose, uric acid, β2-microglobulin and other non-ionic toxins, except urea, can be adsorbed onto the activated carbon 2, removing those toxins from the fluid. Other non-ionic toxins will also be removed by the activated carbon 2. The dialysate or fluid then continues through the sorbent cartridge 1 to the hydrous zirconium oxide layer 3. The hydrous zirconium oxide layer 3 can remove phosphate and fluoride anions, exchanging them for acetate anions. The fluid can continue to move through the sorbent cartridge 1 into the alumina/urease layer 4. Urease can catalyze the reaction of urea to form ammonia and carbon dioxide. The result of this is the formation of ammonium carbonate. The phosphate anions present in the fluid can also be exchanged for hydroxide ions on the alumina. As the fluid continues through the sorbent cartridge 1, the fluid reaches alumina layer 5. The alumina layer 5 can remove any remaining phosphate ions from the fluid and help retain urease within the sorbent cartridge 1, and in certain configurations this layer can exchange urea for ammonium and other components. The last layer through which the fluid travels can be the zirconium phosphate layer 6. In the zirconium phosphate layer 6, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the zirconium phosphate layer 6. The ratio of sodium to hydrogen ions released depends on the ratio originally present in the zirconium phosphate layer 6, and is therefore controllable. The result of the fluid passing through the sorbent cartridge 1 is that the fluid can be regenerated to form clean dialysate that can be safely passed back through a dialyzer to a patient. In any embodiment, potassium, calcium, and magnesium can be added to the clean dialysate to replace any ions which were removed by the sorbent cartridge. The ions can be added and/or controlled via an infusate system that can be positioned on a section of the fluid flow path after the sorbent cartridge.

Figure 7A:
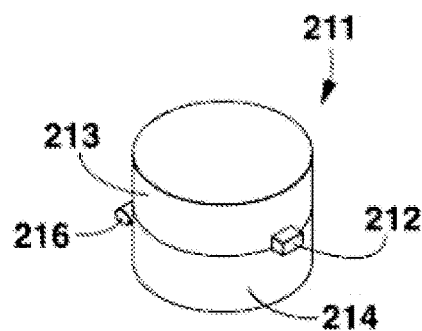
FIG. 7a is a perspective view of a sorbent pouch having the ability to open and reclose via a hinge and a latch member.

In some embodiments, the sorbent pouches of the present invention may be designed so that they can be opened, as shown in FIG. 7a. Top portion 213 of the sorbent pouch 211 and bottom portion 214 of the sorbent pouch 211 may be connected by a hinge 216 and a latch member 212. When latch member 212 on the top portion 213 of sorbent pouch 211 is engaged with flange 215 (shown in FIG. 7b) on bottom portion 214 of the sorbent pouch 211, the top portion 213 of the sorbent pouch 211 can be firmly sealed to the bottom portion 214 of the sorbent pouch 211. When latch member 212 of the sorbent pouch 211 is disengaged from flange 215, top portion 213 can pivot on hinge 216 to separate from bottom portion 214. The sorbent material (not shown) within the sorbent pouch 211 can then be removed in order to be discarded or recharged. The sorbent pouch 211 itself may be reused. The sorbent pouch 211 can be closed by pivoting the top portion 213 of the sorbent pouch 211 so that top portion 213 and bottom portion 214 meet, and reengaging latch member 212 on the top portion 213 of the sorbent pouch 211 with flange 215 on the bottom portion 214 of the sorbent pouch 211. Any type of connection between the top portion 213 and bottom portion 214 of the sorbent pouch 211 is contemplated by this invention. For example, the top portion of the sorbent pouch may include multiple latches (not shown) in the absence of a hinge member, while the bottom portion of the sorbent pouch can include engagement members. When the top portion is placed onto the bottom portion and twisted, the latches can engage the engagement members, creating a connection that can be resistant to inadvertent opening. In order for the connection to be broken, the top portion of the sorbent pouch can be twisted in the opposite direction, allowing the two portions to separate.

In other embodiments, the sorbent pouches may be constructed so that they cannot easily be opened. In such embodiments, the sorbent pouches can be completely sealed to form a complete enclosure around the sorbent material. During construction of the sorbent pouch, once the sorbent material is added, the sorbent pouch can be sealed by any possible means. The sorbent pouches can be heat sealed to fuse the edges of the sorbent pouch together. Alternatively, an adhesive may be used to connect the edges together. In embodiments where a fiber is used to construct the sorbent pouches, the edges may be sewn or woven together to create a sealed sorbent pouch. Any type of chemical or mechanical closure to form the sorbent pouches is contemplated by this invention.

Figure 7B:
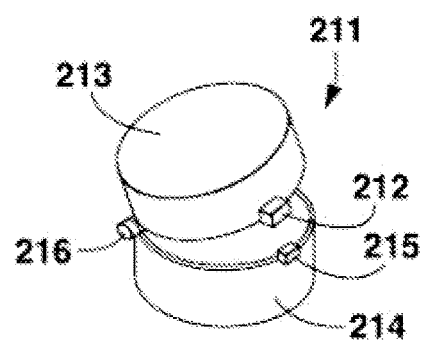
FIG. 7b is a perspective view of a sorbent pouch in an open state.
Figure 8A:
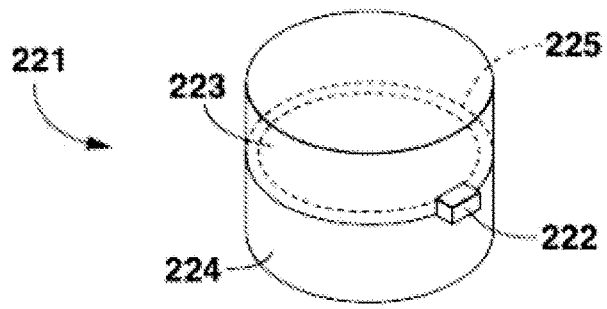
FIG. 8a is a perspective view of a sorbent pouch having an internal sealing ring.
Figure 8B:
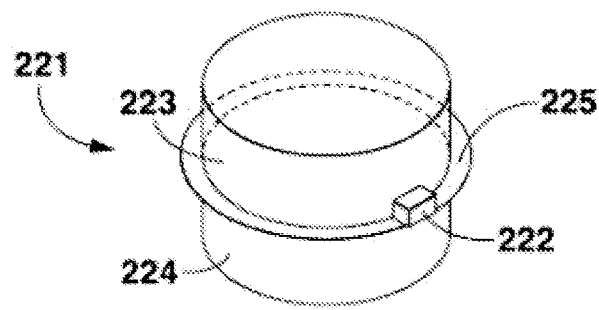
FIG. 8b is a perspective view of a sorbent pouch having an external sealing ring.

In some embodiments, as shown in FIGS. 8a and 8b, the sorbent pouches may have an interior or exterior ring 225 disposed inside of or around the sorbent pouch 221, respectively, creating an additional sealing member to secure the top portion 223 of the sorbent pouch 221 to the bottom portion 224 of the sorbent pouch 221. The coupled surfaces of the rings may be coated in an adhesive material, or the rings may be attached by any other known coupling means. In some embodiments, the rings may be welded. In other embodiments, the rings may be mechanically attached to the sorbent pouches such as with rivets, screws or clamps. In another embodiment, engagement hooks may be placed on the rings, wherein the engagement hooks can attach to the sorbent pouch in a similar fashion as described for connecting the top and bottom portions of the sorbent pouches as shown in FIGS. 7a and 7b.

Figure 9:
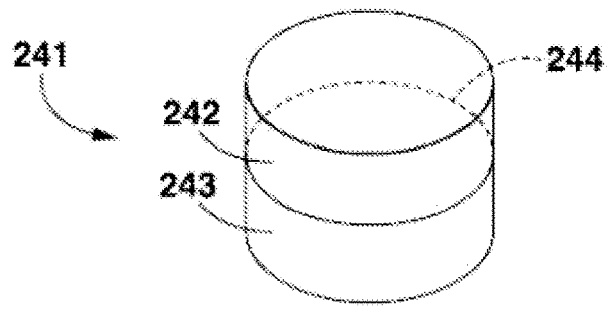
FIG. 9 is a perspective view of a sorbent pouch with an internal separator.

In some embodiments, such as that shown in FIG. 9, a single sorbent pouch can contain multiple sorbent materials. Sorbent pouch 241 can comprise a separator 244 disposed within the sorbent pouch. The separator 244 can run through the entire interior space of the sorbent pouch 241. The separator 244 creates, within the sorbent pouch 241, a top portion 242 and a bottom portion 243, which are kept completely separate from each other. One sorbent material may be placed in the top portion 242 of the sorbent pouch 241, and a different sorbent material may be placed in the bottom portion 243 of the sorbent pouch 241. This allows two different materials to be placed within a single sorbent pouch 241, but still remain separate from one another. In another embodiment, two or more sorbent materials can be placed in a single sorbent pouch without a separator (not shown). The sorbent materials may be arranged in layers within the sorbent pouch, or may be intermixed. The separator 244 can be constructed from the same material as the sorbent pouch 241 itself, or may be a different material that still allows fluid to pass through the separator 244 freely, while preventing passage of the sorbent material.

In other embodiments, more than one separator can be used within a single sorbent pouch. The present invention contemplates sorbent pouches containing 2, 3, 4 or more separators within a single sorbent pouch.

In other embodiments, multiple sorbent materials can be mixed within a sorbent pouch. Mixing different sorbent materials together can be accomplished without a loss in efficiency of the sorbent materials.

Figure 10:
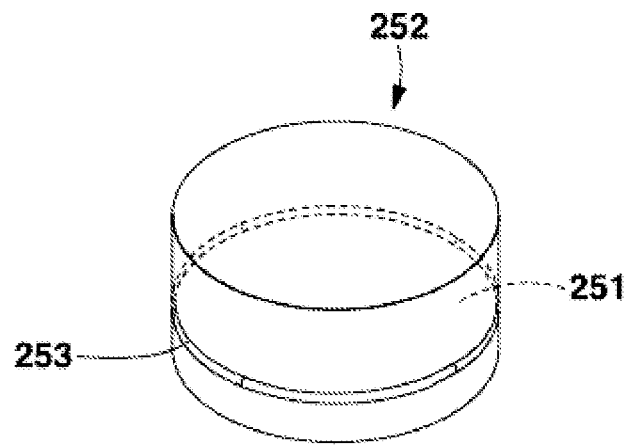
FIG. 10 is a perspective view of a sorbent pouch with an o-ring seal member.

The sorbent pouches of the present invention can have a mechanism to create a seal between the sorbent pouch and the inner surface of the sorbent cartridge in which the sorbent pouch is placed, such that fluid is kept from flowing around the sorbent pouch and instead is directed into the sorbent pouch. FIG. 10 shows one non-limiting embodiment of a seal mechanism. A flexible sorbent pouch 251, such as one made out of a fiber, can be placed inside of a sorbent cartridge 252. In other embodiments, the sorbent pouch may be made out of a rigid material, such as a polymer or metal. In order to avoid a situation in which spent dialysate flows around the sorbent pouch 251 and therefore does not contact the sorbent material inside the sorbent pouch 251, the sorbent pouch 251 may be sealed to the sorbent cartridge 252. O-ring 253 placed on the circumference of sorbent pouch 251 can form a seal with the sorbent cartridge 252 so as to prevent spent dialysate from flowing around the sorbent pouch 251, and instead directing spent dialysate through the sorbent pouch 251. The sorbent pouch 251 may be filled so that the circumference of the sorbent pouch 251 is slightly wider than that of the sorbent cartridge 252. This will ensure that the sorbent pouch 251 covers the entire inner area of the sorbent cartridge 252 and that there are no spaces for fluid to pass by without flowing through the sorbent pouch 251. O-ring 253 can also serve to ensure that sorbent pouch 251 keeps the intended shape by providing a semi-rigid border.

Figure 11:
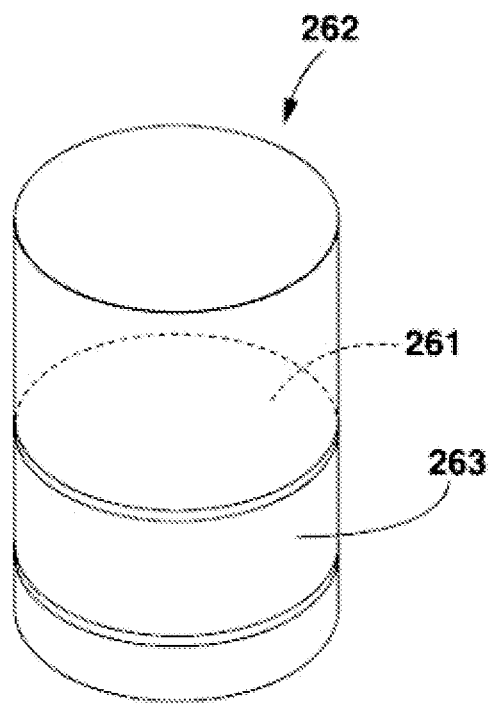
FIG. 11 is a perspective view of a sorbent pouch with an elastomeric material on the side walls.

In an alternative embodiment, shown in FIG. 11, an elastomeric material 263 may be disposed on the edges of the sorbent pouch 261. When the sorbent pouch 261 is placed in the sorbent cartridge 262, the elastomeric material 263 functions like the o-ring described above to create a seal and keep liquid from flowing around the sorbent pouch 261. The elastomeric material 263 can be made to completely cover the outside edges of the sorbent pouch 261, or the elastomeric material can be disposed in one or more thin strips of material. Alternatively, the inside walls of the sorbent cartridge may be coated in an elastomeric substance, which will function to form the same seal when a rigid or semi-rigid sorbent pouch is placed within. In any embodiment, the sorbent pouches may be constructed to be slightly larger than the sorbent cartridge. When the user inserts the sorbent pouches into the sorbent cartridge, the sorbent pouches can be compressed slightly to fit in the sorbent cartridge. This will ensure that the sorbent pouches cover the entire area inside the sorbent cartridge and facilitate the formation of a seal around the edges of the sorbent pouch.

Figure 12:
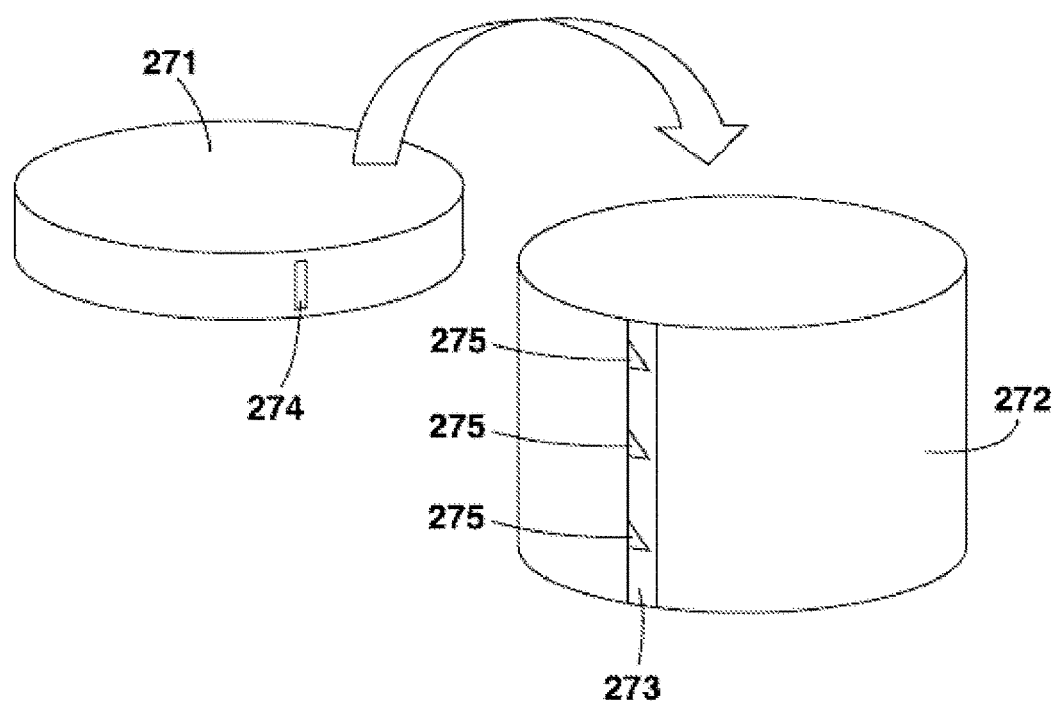
FIG. 12 is a perspective view of a sorbent pouch and cartridge with a key function to ensure correct alignment.

In some embodiments, it may be important to ensure that the sorbent pouches are properly inserted into the sorbent cartridge. Any method of doing so is contemplated by this invention. One non-limiting example is shown in FIG. 12. Groove 273 may be created in the wall of the sorbent cartridge 272. A key 274, or flange, may be disposed on the side of the sorbent pouch 271. In order for the sorbent pouch 271 with key 274 to fit within the sorbent cartridge 272, the key 274 must be aligned with groove 273 in the sorbent cartridge 272 wall. This will ensure that the sorbent pouch 271 is disposed within the sorbent cartridge 272 with the correct alignment. In some embodiments, optional ridges 275 may be placed within groove 273. The ridges 275 can serve to lock the sorbent pouch 271 in place vertically within the sorbent cartridge 272. The ridges 275 may be designed so that they are angled on the top portion of the ridge 275 and flat on the bottom portion of the ridge 275. Once the key 274 passes a ridge 275 in a downward direction, the ridge 275 can serve to keep the sorbent pouch 271 from inadvertently moving back upward within the sorbent cartridge 272.

The ridges 275 may be designed such that the sorbent pouch 271 may be removed upward from the sorbent cartridge 272 only with the use of force greater than would be expected from inadvertent moving but not so much force as to prevent intentionally lifting the sorbent pouch out of the sorbent cartridge 272. This can be accomplished by using a semi-rigid material as either the key 274, the ridges 275, or both, such that when enough force is applied the key 274 or ridges 275 can be bent far enough to allow removal of the sorbent pouch 271, after which the key 274 or ridges 275 can return to their original shape. Alternatively, the ridges 275 may be attached with a spring mechanism that is connected to a button (not shown), such that when the button is depressed the ridges 275 recede into the interior wall of the sorbent cartridge 272 and allow easy removal of the sorbent pouch 271 from the sorbent cartridge 272.

In other embodiments, the sorbent pouches may be loosely contained within the sorbent cartridge. The sorbent pouches need not be made the same size as, or larger than, the sorbent cartridge. One or more sorbent pouches may be constructed of a smaller size than the interior circumference of the sorbent cartridge, and may be simply placed in the sorbent cartridge.

After construction of the sorbent pouch containing a sorbent material or materials, the material within the sorbent pouch can be washed so as to remove any particles smaller than the pore or mesh size of the sorbent pouch material. This will ensure that all particles within the sorbent pouch are large enough so that they cannot inadvertently pass out of the sorbent pouch. Thus, when used in a sorbent cartridge, the sorbent pouches themselves can act as a particulate filter, ensuring that no particulate matter of the sorbent material, or any other particulate matter, can pass downstream. This may eliminate the need for the use of external particulate filters.

In some embodiments, antimicrobial or antibacterial material may be impregnated into the sorbent pouch. This allows sterilization of the dialysate as the dialysate flows through the sorbent cartridge, and can eliminate the need for antimicrobial filters. In other embodiments, medication such as heparin or other anticoagulants, or antibiotics may be impregnated into the sorbent pouch. This can allow administration of these medications to the patient without the need for adding the drugs to the dialysate.

Figure 13:
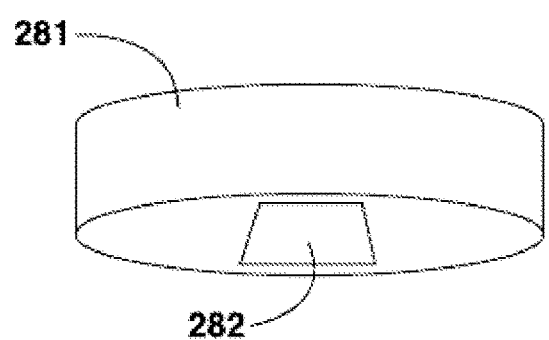
FIG. 13 is a perspective view of a sorbent pouch with a double layer of material in the center to control flow through the sorbent pouch.

In some embodiments flow throughout the sorbent pouch can be controlled by variations in the sorbent pouch material. Generally, fluid moving through a conduit will move most quickly through the center of the conduit, and more slowly towards the edges. To ensure that fluid travels more evenly throughout the sorbent pouch, the sorbent pouch can be constructed such that more fluid enters the sorbent pouch on the outer edges of the sorbent pouch than enters in the center. One non-limiting example is shown in FIG. 13. A sorbent pouch 281, such as one made out of a fabric or other flexible material, can be constructed with an extra layer of fabric or other flexible material 282 in the center of the bottom face of the sorbent pouch 281. This extra layer of fabric 282 effectively reduces the mesh size of the sorbent pouch in that location. With a smaller mesh size, resistance to flow will be greater in the center of the sorbent pouch 282, and fluid flow will be more evenly distributed to the edges of the sorbent pouch 282. In embodiments where the sorbent pouch is made out of metal or a polymer, the same effect can be created by making a smaller pore size, or alternatively less pores, in the center of the sorbent pouch. In other embodiments, a separator, similar to the one shown in FIG. 9, can be utilized in the middle of the sorbent pouch. The separator can be constructed as described above, such as with an extra layer of fabric near the center, to better control the flow of fluid throughout the sorbent pouch. Although shown in FIG. 13 as a centrally positioned rectangular layer, the extra layer of fabric 282 or other material may be positioned anywhere along the outer surface of the sorbent pouch 281, and may take any shape, such as circular, rectangular, triangular, etc such that flow dynamics are altered.

In some embodiments, a patterned flow of fluid through the sorbent cartridge can be created. Occlusions, or blockages, of some of the pores can result in restricted flow through some portions of the sorbent pouch. In some embodiments, some of the pores in the sorbent pouch may be larger or smaller than other pores in the rest of the sorbent pouch. Flow will be increased through the larger pores as compared to the smaller pores, allowing control over fluid flow into and out of the sorbent pouch. Fluid flows through sorbent materials of varying particle sizes and granular diameters at various rates and pressures. Fluid flows at a higher rate and at a lower pressure through granules of larger diameter, while fluid flows at a slower rate and at a higher pressure through granules of smaller diameter. Wicking can occur when fluid generally flows in the direction of areas of least pressure. For example, fluid flow through a fine particle sorbent material, such as zirconium phosphate, can result in wicking. In such an instance, the fluid has a tendency to flow towards an area of lower resistance, generally near the wall of the container. This can result in the fluid not flowing through a large portion of the sorbent material, such that the fluid is not coming into contact with the sorbent materials. To ensure that fluid flows through the sorbent pouch and the sorbent materials more evenly, the sorbent pouches of the present invention can be constructed such that fluid is directed to flow away from the walls of the sorbent pouch and towards the interior of the sorbent pouch.

Figure 15:
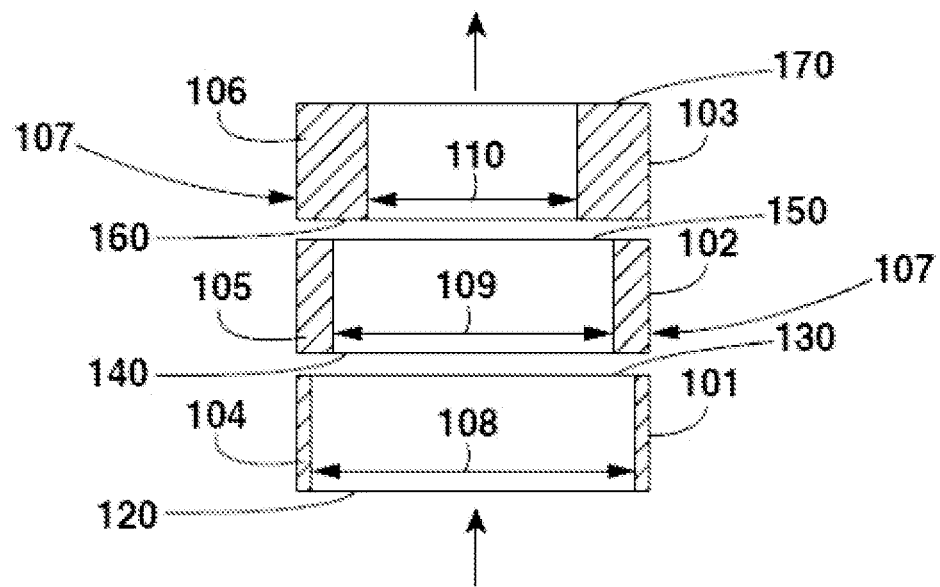
FIG. 15 shows an exploded cross-sectional view of a sorbent cartridge having stacked sorbent pouches, with each sorbent pouch in series having a thicker sidewall, and therefore smaller interior diameter, than that of the previous sorbent pouch in series.

In some embodiments, flow of fluid through the sorbent pouches can be controlled by varying the interior diameters of the sorbent pouches. In FIG. 15, the second sorbent pouch 102 has an interior wall 105 that is thicker than the interior wall 104 of the first sorbent pouch 101, such that the interior diameter 109 of the second sorbent pouch 102 is smaller than the interior diameter 108 of the first sorbent pouch 101. Similarly, the third sorbent pouch 103 has an interior wall 106 that is thicker than the interior wall 105 of the second sorbent pouch 102, such that the interior diameter 110 of the third sorbent pouch 103 is smaller than the interior diameter 109 of the second sorbent pouch 102. Each sorbent pouch can have a wall that is thicker than that of the immediately preceding sorbent pouch in a direction from the bottom surface 120 of the first sorbent pouch 102 to the top surface 170 of the third sorbent pouch 103 while maintaining a substantially identical outer diameter among each sorbent pouch. Any number of sorbent pouches can be used in any embodiment of this invention. Fluid flowing through the bottom surface 120 of the first sorbent pouch 101 to the top surface 130 of first sorbent pouch 101, through the bottom surface 140 and top surface 150 of the second sorbent pouch 102, and through the bottom surface 160 to the top surface 170 of the third sorbent pouch 103, is directed into the interior space of each pouch sequentially. Because each sorbent pouch has a thicker wall than the preceding sorbent pouch in series, each sorbent pouch has a smaller effective area through which fluid can flow than the preceding sorbent pouch. This gradually decreasing flow area will result in pushing the fluid moving from one sorbent pouch to another sorbent pouch along the edges of the sorbent pouches near the wall of the sorbent cartridge 107 towards the center of the subsequent sorbent pouch. In one embodiment, the wall of each sorbent pouch can be between 5-10% thicker than the wall of the preceding sorbent pouch. In other embodiments, the thickness of the wall of each sorbent pouch can be between 1-5%, 10-15%, 15-20% or 20-30% thicker than the wall of the preceding sorbent pouch.

Figure 16:
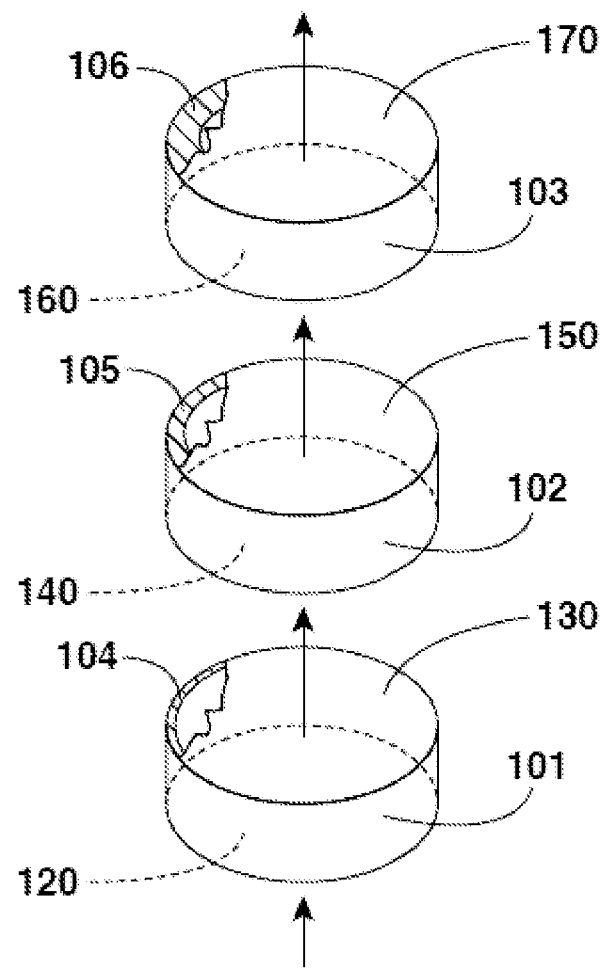
FIG. 16 shows an exploded perspective view of a sorbent cartridge having stacked sorbent pouches, with each sorbent pouch in series having a thicker sidewall, and therefore smaller interior diameter, than that of the previous sorbent pouch

FIG. 16 is an exploded view of FIG. 15. As can be seen, fluid flowing up through the first sorbent pouch 101 through sorbent pouches 102 and 103 will be pushed toward the center of each sorbent pouch by the thickening side walls of each sorbent pouch in series.

Figure 17:
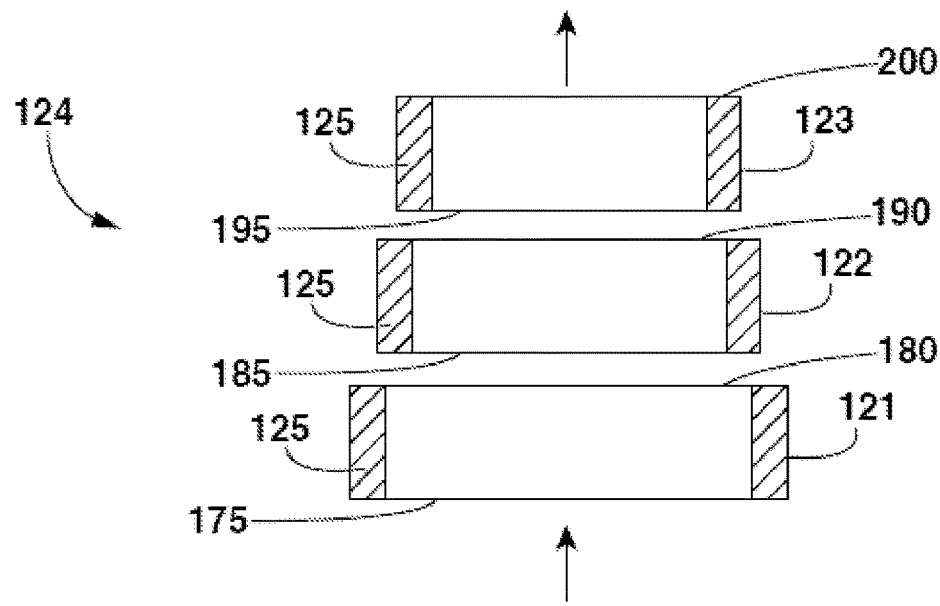
FIG. 17 shows an exploded cross-sectional view of a sorbent cartridge having stacked sorbent pouches, with each sorbent pouch in series having a smaller exterior diameter than that of the previous sorbent pouch.

In an alternative embodiment, each sorbent pouch may be constructed with a smaller outside diameter than that of the preceding sorbent pouch. Constructing each sorbent pouch with a smaller diameter and the same wall thickness as the previous sorbent pouch will create the same effect as constructing each sorbent pouch with a progressively thicker wall. In some embodiments, as shown in FIG. 17, the interior diameter of the sorbent cartridge 124 can also decrease to accommodate each sorbent pouch. The first sorbent pouch 121 can have the largest diameter of all the sorbent pouches and can be placed in the sorbent cartridge 124 where the interior diameter of the sorbent cartridge 124 is the largest. Second sorbent pouch 122 can have a smaller diameter than first sorbent pouch 121 and can be placed in the sorbent cartridge 124 where the interior diameter of the sorbent cartridge 124 is smaller. Third sorbent pouch 123 can have a smaller diameter than second sorbent pouch 122 and can be placed in the sorbent cartridge 124 where the interior diameter of the sorbent cartridge 124 is smallest. The wall thickness 125 of each sorbent pouch can be constant. In any embodiment, more than three sorbent pouches can be used, and the sorbent cartridge 124 can have more than three different sized interior diameters. In this embodiment, fluid can flow up through bottom surface 175 and top surface 180 of first sorbent pouch 121, through bottom surface 185 and top surface 190 of second sorbent pouch 122, and through bottom surface 195 and top surface 200 of third sorbent pouch 123 such that the fluid is passing through a constricting area with each subsequent sorbent pouch, and accordingly is pushed toward the center of each sorbent pouch.

Figure 18:
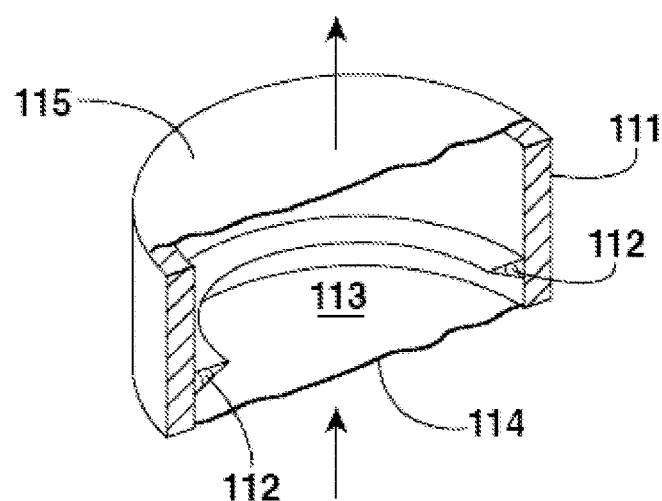
FIG. 18 shows a cross-sectional perspective view of a sorbent pouch having an annular ring disposed on the interior circumference of the sorbent pouch.

In other embodiments, as shown in FIG. 18, annular rings or "o-rings" may be used to direct flow of fluid into the center of the sorbent pouch. A sorbent pouch 111 can have an annular ring 112 placed and adhered by any known means around the interior circumference of the sorbent pouch 111. The cross-section of the annular ring 112 can be angled so that the annular ring 112 extends radially into the interior 113 of the sorbent pouch 111. The angle of the annular ring 112 can direct fluid entering the bottom 114 of the sorbent pouch 111 from the area near the edge of the sorbent pouch 111 into the interior 113 of the sorbent pouch 111 as the fluid exits through the top surface 115 of the sorbent pouch 111. In other embodiments, the annular ring can have a curved shape. Alternatively, the annular ring can have a rectangular shape. In some embodiments, each sorbent pouch can include multiple annular rings. For example, a sorbent pouch may have 2, 3, 4, 5, 6, or more annular rings spaced along the interior circumference of the sorbent pouch to continuously push fluid into the center of the sorbent pouch as the fluid passes through the sorbent pouch. The annular rings may be made out of any substance known in the art. In some embodiments, the annular rings may be constructed from an elastomeric material, such as the o-rings described above. In other embodiments, the annular rings may be constructed from plastic or some other inert material. In one embodiment, the annular rings may extend inwardly towards the center of the sorbent pouch at a length of between 5-10% of the diameter of the sorbent pouch. In other embodiments, the annular rings may extend between 1-5%, 10-15%, 15-20% or 20-30% of the diameter of the sorbent pouch.

One skilled in the art will understand that various combinations and/or modifications and variations can be made in the sorbent pouches and systems depending on the specific needs for operation. Moreover, features illustrated as being part of an aspect of the invention can be included in the aspect of the invention, either alone or in combination.

We claim:

1. A sorbent pouch, comprising:
a porous material forming in-part a sorbent pouch containing a sorbent material consisting essentially of urease, the porous material allowing fluid to pass through the pouch and substantially retaining urease in solution in the sorbent pouch.

2. The sorbent pouch of claim 1, wherein the porous material retains greater than 98% by weight of the urease in solution.

3. The sorbent pouch of claim 1 wherein the porous material is selected from the group consisting of bolting cloth, porous polymer, porous metal, cotton, ashless filter paper, Dacron, and polyethylene terephthalate.

4. The sorbent pouch of claim 1, wherein the sorbent pouch has a shape selected from the group consisting of the circular shape, the square shape, a triangular shape, a rectangular shape, and a disc shape.

5. The sorbent pouch of claim 4, wherein the sorbent pouch is shaped to be adapted into an internal cavity defined by a sorbent cartridge in which the sorbent pouch is housed.

6. The sorbent pouch of claim 1, wherein the sorbent pouch has a semi-rigid structure.

7. The sorbent pouch of claim 1 wherein the sorbent pouch has a rigid structure.

8. The sorbent pouch of claim 1 further comprising side portions constructed from a fluid impermeable material.

9. The sorbent pouch of claim 1 wherein the porous material is impregnated with an antimicrobial substance and/or an anticoagulant.

10. The sorbent pouch of claim 1, wherein the sorbent pouch further comprises an o-ring seal member disposed on an outer periphery of the pouch.

11. The sorbent pouch of claim 1, wherein at least one portion of the sorbent pouch comprises a double layer of the pouch material.

12. The sorbent pouch of claim 1 wherein the sorbent pouch can be opened and re-sealed.

13. The sorbent pouch of claim 8 further comprising an elastomeric material disposed on a side portion of the pouch.

14. The sorbent pouch of claim 1, wherein the sorbent pouch and a second pouch have a repeating geometric shape.

15. The sorbent pouch of claim 1, wherein the sorbent pouch has a smaller pore size or less pores in a center of the sorbent pouch than outer edges of the sorbent pouch.

16. The sorbent pouch of claim 1, wherein the sorbent pouch is connected to a dialysis flow path.

17. A sorbent pouch system, comprising:
one or more sorbent pouches formed from a porous material containing inside at least one sorbent material wherein the porous material allows fluid to pass through the one or more pouches; and
the one or more pouches are capable of being attached and/or detached from each other;
wherein at least one sorbent pouch contains a sorbent material consisting essentially of urease and comprises a porous material allowing fluid to pass through the pouch and substantially retaining urease in solution in the sorbent pouch.

18. The sorbent pouch system of claim 17, wherein each of the one or more pouches comprises any of:
i) sidewalls having a thickness different from that of the other pouches, such that the one or more pouches have differing interior diameters; wherein the one or more pouches are placed in series, and wherein each pouch has a sidewall thickness greater than that of the previous pouch in series;
ii) a differing exterior diameter from the other pouches; wherein the one or more pouches are placed in series, and wherein each pouch has an exterior diameter smaller than that of the previous pouch in series; and
iii) one or more annular ring, wherein the one or more annular ring is constructed from a fluid impermeable substance, and wherein the annular ring is disposed on the interior circumference of the sorbent pouch and extends radially into the center of the sorbent pouch; wherein the annular ring has a cross-sectional shape selected from the group comprising circular, triangular, and rectangular.

* * * * *